Figure 1:
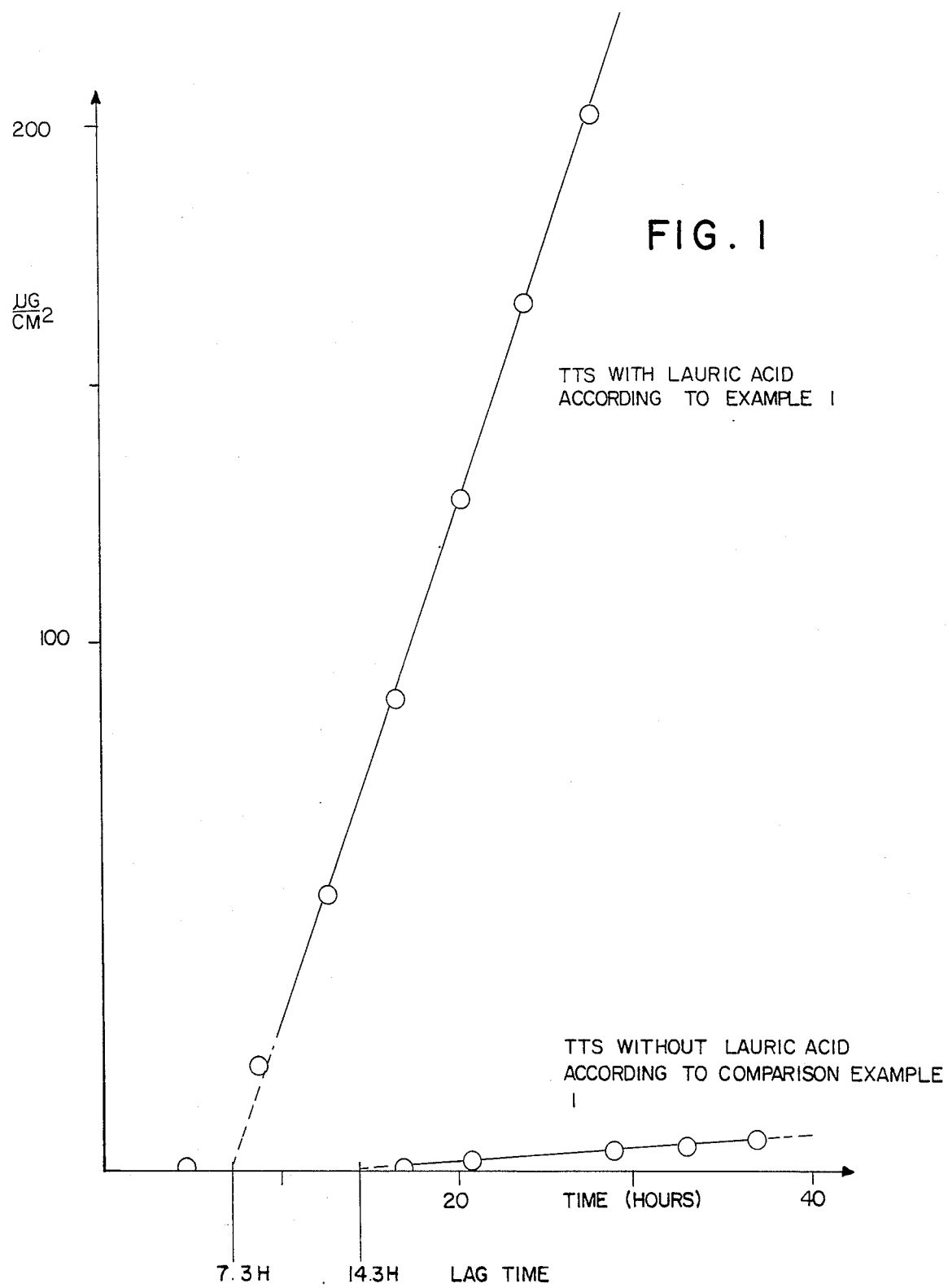

United States Patent [19]

Guse et al.

[11] Patent Number: 4,882,163

[45] Date of Patent: Nov. 21, 1989

[54] TRANSDERMAL THERAPEUTIC SYSTEM

[75] Inventors: Günter Guse, Hamburg; Michael Horstmann, Neuwied; Axel Erler, Hamburg, all of Fed. Rep. of Germany

[73] Assignee: Beiersdorf Aktiengesellschaft, Hamburg, Fed. Rep. of Germany

[21] Appl. No.: 226,631

[22] Filed: Aug. 1, 1988

[30] Foreign Application Priority Data

Sep. 2, 1987 [DE] Fed. Rep. of Germany ....... 3729299

[51] Int. Cl.$^4$ ............................................. A61F 13/02
[52] U.S. Cl. ..................................... 424/448; 424/449
[58] Field of Search ................. 424/448, 449; 574/946

[56] References Cited

U.S. PATENT DOCUMENTS 4,525,339  6/1985  Behl et al. ........................... 424/480
4,778,678 10/1988  Guse et al. ........................... 424/449

Primary Examiner—Thurman K. Page
Assistant Examiner—Leon R. Horne
Attorney, Agent, or Firm—Sprung Horn Kramer & Woods

[57] ABSTRACT

Transdermal therapeutic system for administration of moxonidine, containing at least one higher n-alkane-carboxylic acid with at least 12 C atoms as a permeation accelerator.

8 Claims, 2 Drawing Sheets

TRANSDERMAL THERAPEUTIC SYSTEM

The invention relates to a transdermal therapeutic system for administration of moxonidine.

Transdermal medicaments are known. The main advantages which this presentation form can have specifically for medicament substances with a systemic action are also undisputed, such as, for example, relieving the load on the gastrointestinal tract, increasing the bioavailability or avoiding undesirable peak blood level values.

On the other hand, the permeability of the skin to medicament substances is limited. It is more the exception than the rule that a medicament substance diffuses from an acceptably small application area through the horny layer of the skin in an amount such that therapeutically relevant blood levels are produced. Such an exception is glycerol trinitrate, for which transdermal administration from a plaster is known and is described, inter alia, in DE-OS 3,518,707.

There has been no lack of attempts also to administer other medicament substances transdermally, for example in the form of ointments, creams or sprays or as plasters. Apart from a few exceptions, large application areas are thereby required, as these counteract convenient and reliable use and can thus in the end impair therapy compliance.

The centrally active antihypertensive moxonidine, chemical name 4-chloro-5-(imidazolin-2-ylamino)-6-methoxy2-methylpyrimidine, the transdermal medicament form of which is described in EP-A 169,364, also requires an exceptionally large area of plaster according to this prior art.

There have thus been various proposals for increasing the permeability of the skin in the desired manner by using pharmaceutical auxiliaries. These are often called permeation accelerators, penetration promoters or penetration enhancers, and are called enhancers for short below.

Enhancers which are mentioned according to the prior art are:

Alcohols in German Pat. No. 2,135,533, DE-OS 3,205,258, EP-A 182,635 and EP-A 131,228, aliphatic esters in U.S. Pat. Specification No. 4,336,243, German Pat. No. 2,135,533 and U.S. Pat. No. 4,390,520 and amides in U.S. Pat. No. 3,742,951, German Pat. No. 2,604,718 and EP-A 95,169, glycerol esters in U.S. Pat. No. 4,336,243 and U.S. Pat. No. 4,552,751 and sulphoxides in German Pat. No. 2,755,661 and DE-OS 3,614,843.

Organic acids have also been described as penetration improvers, in particular together with alcohols or glycols, by E.R. Cooper et al.; J. Pharm. Sci. 74, 688 (1985), and in DE-OS 3,528,979 and EP-A 171,742.

Experimental evidence that the above-mentioned enhancers act in the desired manner, that is to say lead to therapeutically relevant permeations which are significantly increased in comparison with the enhancer-free system, with acceptably small areas of use, is as a rule lacking. When used as plasters of the matrix type, such as often claimed, there is also the difficulty that pharmaceutical and adhesive requirements have to be taken into consideration to the same degree, and quality-stable and reliable production, storage and use of the finished medicament form, and finally also the physiological acceptability of the enhancers used in interaction with the adhesive composition and the like is to be guaranteed.

The object of the present invention was thus to develop a transdermal therapeutic system for moxonidine, as a medicament substance with limited access through the skin, which does not have the disadvantages of products according to the prior art and with which, in addition, (a) the lag time before the active compound enters the circulation is shortened, (b) the rate of absorption per unit area to be measured from then on is increased and (c) the rate of absorption of the active compound at the end of the lagtime remains largely constant.

The entire system should moreover be physiologically acceptable.

In other words, the object was to bring a relatively polar medicament substance, that is to say moxonidine, through the stratum corneum with an increased flow rate per unit time and area. Its permeation properties are largely determined by the hydrophobic ordered structures of the micellar "cement phase" of this layer. It was obvious to the expert to consider as enhancers those substances which have a certain lipid similarity, that is to say, for example, triglycerides or phosphatides. In contrast, this did not have the desired success in practice.

Surprisingly, however, it has been found that a completely different type of substance, that is to say a higher n-alkanecarboxylic acid with at least 12 C. atoms, are particularly suitable enhancers for the aminic medicament substance moxonidine.

Preferred n-alkanecarboxylic acids are those with 12–18 C. atoms, above all myristic acid, palmitic acid and especially lauric acid.

Figure 2:
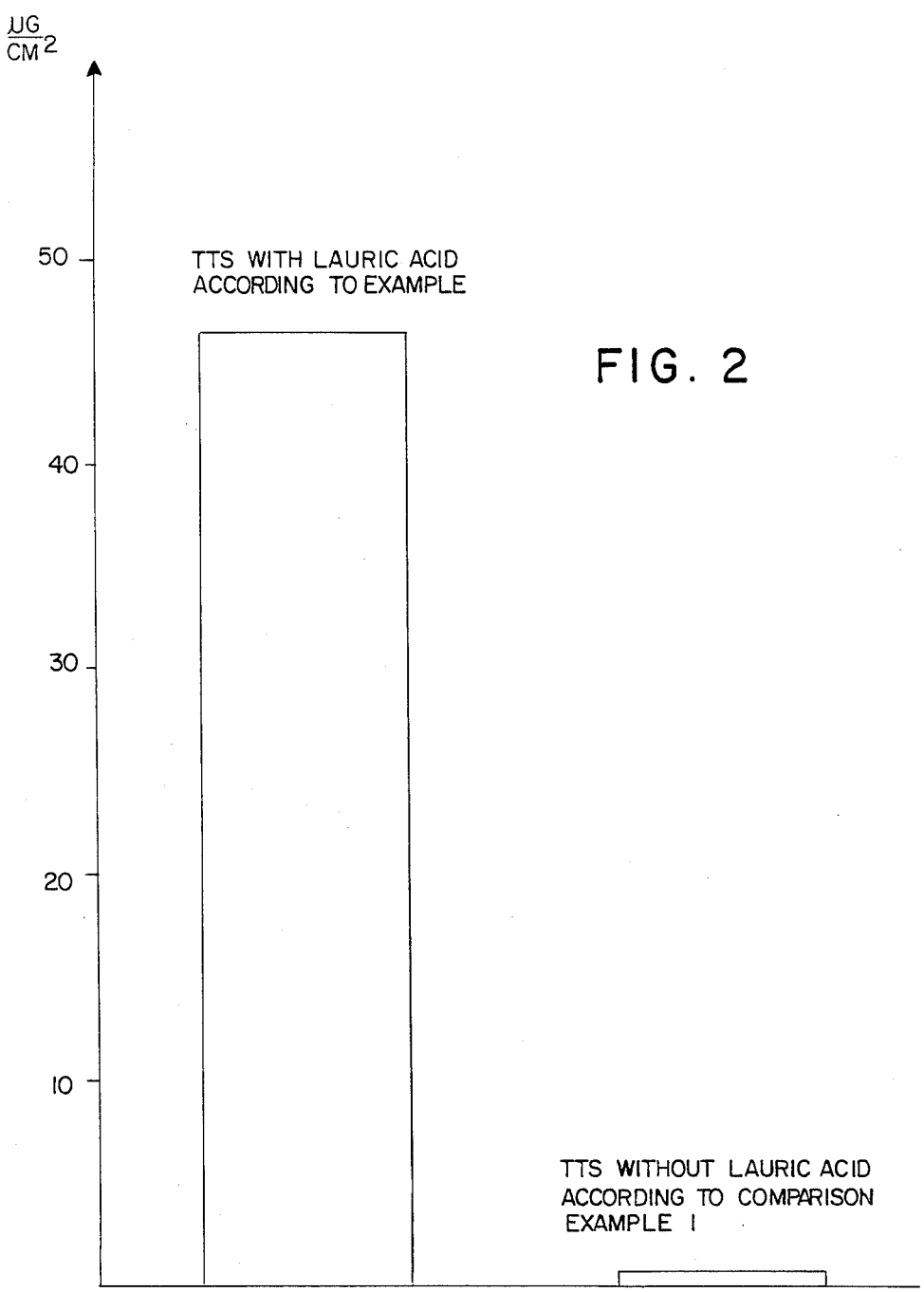

Lauric acid shortens the lag time of moxonidine in vitro by about half in comparison with the corresponding enhancer-free system (compare FIG. 1). A steady state then starts; the release curve becomes a straight line. The transdermal flow is increased by a factor of about 35. This pattern is confirmed in the in vivo experiment (FIG. 2).

The transdermal therapeutic system according to the invention is moreover suitable for producing a uniform transdermal flow from a single plaster for several days, in particular 3 or more days. Treatment of high blood pressure for several days thus becomes possible, without having to change the plaster.

The n-alkanecarboxylic acids used, in particular lauric acid (n-dodecanoic acid), myristic acid (n-tetradecanoic acid) and palmitic acid (n-hexadecanoic acid), but above all lauric acid, in fact occupy a special position as enhancers according to the invention. Not only are the enhancers mentioned of different chemical structure unsuitable for the purpose according to the invention, the shorter fatty acids of the type used are also of little suitability for the transdermal therapeutic system according to the invention, because with these the requirement of skin penetration increases further with time and does not reach equilibrium, so that a uniform rate of penetration cannot be achieved with these.

Transdermally active plasters according to the invention can be designed either as reservoir systems with a control membrane or as matrix systems in which a self-adhesive composition already contains the active compound and enhancer. The latter are preferred according to the invention because of their simple build-up and the resulting high production and medicament reliability.

In the case of plasters as the transdermal therapeutic system according to the invention, which are preferable to ointments, creams or sprays, preferably about 5–10 g of moxonidine and about 7–20 g of n-alkanecarboxylic acid, such as lauric acid, myristic acid or palmitic acid, are used per square meter. If desired, the acids used according to the invention can thereby be used individually or as a mixture. Lauric acid is preferably predominantly present, in particular with more than 50% by weight of the enhancer used. A content of about 5–10 g moxonidine and 7–15 g of lauric acid per square meter is particularly preferred. The weight ratio of moxonidine to enhancer in a transdermal therapeutic system according to the invention, in particular plasters, is furthermore preferably 1:1 to 1:2.

The choice of basic self-adhesive compositions for transdermally active plasters according to the invention is not critical. Any self-adhesive composition which has the required adhesive properties, does not interact undesirably with the active compound and enhancer and releases both substances in the manner described above is suitable. Polyacrylate self-adhesive compositions and those of saturated rubbers and adhesive resins, for example based on polyisobutene and synthetic hydrocarbon resins, are particularly advantageously used.

The active compound and enhancer can be incorporated into the basic polymer by simple mixing with a stirrer, but they are particularly advantageously incorporated in a ball mill by the process of DE-OS P 36 17 158. This treatment leads to a considerable improvement in the particle fineness and wetting of the active compound and auxiliary and thus to an increased homogeneity of the entire system.

The fatty acids used are very active plasticizers for self-adhesive compositions, which can lead to roping and to undesirable residues of adhesive on the skin when the basic polymers which are in themselves already soft are used. With polyacrylates, the cohesion of the matrix can be increased if required by cross-linking without difficulty, particularly advantageously by UV irradiation in accordance with German Pat. No. 2,743,979, and with polyisobutenes this can be effected by using particularly high molecular weight types.

Both occlusively acting films or the like and, particularly advantageously, woven fabric, non-woven fabric or the like which is permeable to air or water vapor can be used as the carrier materials for the self-adhesive plasters containing active compound and enhancer.

Coating of the carrier material, drying, covering with the adhesive protective film and stamping out and packaging of individual plasters can be carried out in accordance with the customary methods for the manufacture of medical plasters. The invention is illustrated in more detail below by means of examples.

EXAMPLE 1

A basic polymer of 18.5% by weight of n-butyl acrylate, 78.2% by weight of 2-ethylhexyl acrylate, 2.8% by weight of acrylic acid and 0.5% by weight of benzoin acrylate is prepared by free radical solution polymerization in accordance with German Pat. No. 2,743,979.

65 g of this basic polymer, dissolved in benzine/acetone, 15 g of micronized moxonidine base and 20 g of lauric acid are introduced into a hard porcelain ball mill and the total solids content is brought to 35% by weight with ethyl acetate. The closed ball mill is rotated on a roll bench at about 25 revolutions/minute for 24 hours. The homogenized formulation can then be removed as a self-adhesive composition ready for brushing. It is brushed onto polyester film of 15 micrometer thickness in a coating thickness such that a layer of 50 g/m$^2$ remains after drying at room temperature for 48 hours. It is covered with adhesive protective film.

The self-adhesive matrix thus prepared contains 7.5 g of moxonidine and 10 g of lauric acid per square meter and can be cut into plasters of any desired size.

The methods described below are used to test the plasters according to the invention.

Penetration through excised porcine skin.

A circular piece of porcine skin — about 7 cm in diameter — is freed from residues of subcutaneous fatty and connective tissue. A plaster (16 cm$^2$ area) is freed from the protective film and now stuck onto the outside of the piece of skin. The passage of the active substance through the animal skin is investigated in a phosphate buffer solution (pH 5.5) in a suitable glass apparatus in a waterbath at $34.0 + -0.1°$ C. Samples of the buffer solution are thereby taken at intervals of a few hours, and the active compound content and thus the amount of substance taken up per time and area is determined in these by means of high pressure liquid chromatography. The volume of the buffer solution is adjusted so that "sink" conditions prevail over the entire duration of the experiment (about 40 hours).

FIG. 1 shows the amount of moxonidine absorbed per unit area by the buffer solution in comparison with Comparison Example 1.

Determination of the bio-availability on animals.

A 16 cm$^2$ plaster is stuck onto the lumbar region of a pig with little hair and is left in place for the entire duration of the experiment.

The moxonidine concentration measured in the urine of the animal by means of high pressure liquid chromatography is calculated in relation to the volume released in the collection interval of 24 hours. Since moxonidine is excreted almost exclusively unchanged via the kidney, the absorption rate per square centimeter of plaster shown in FIG. 2 in comparison with Comparison Example 1 is thereby calculated.

EXAMPLE 2

A basic mixture of 31.8% by weight of polyisobutene $M_v = 2,800,000$ (Oppanol B 150), 40.9% by weight of polyisobutene $M_v = 40,000$ (Oppanol B 10), 18.2% by weight of aliphatic hydrocarbon resin with an R+B softening point of 97° C. (Escorez 1202) and 9.1% by weight of heavy liquid paraffin oil (Goldol) in n-heptane is prepared in a kneader.

65 g of the solids of this basic mixture, 15 g of micronized moxonidine base and 20 g of lauric acid are introduced into a hard porcelain ball mill and the total solids content is brought to 33% by weight with n-heptane/ethyl acetate 9:1.

Further processing and testing are carried out in accordance with Example 1.

COMPARISON EXAMPLE 1

A mixture of 81.25 g of the basic polymer according to Example 1, dissolved in benzine/acetone, and 18.75 g of micronized moxonidine base is prepared as in Example 1, ground, brushed on in an amount of 40 g/m$^2$, dried and tested.

The amounts are chosen so that, as in Example 1, 7.5 g of moxonidine are present per square meter and the ratio of moxonidine to basic polymer is also the same as in that example (1:4.33).

The release in vitro and in vivo are determined as in Example 1. The results are shown in FIGS. 1 and 2.

We claim:

1. A tansdermal therapeutic system for administration of moxonidine, comprising moxonidine and at least one higher n-alkane carboxylic acid with at least 12 C. atoms as a permeation accelerator.

2. A transdermal therapeutic system according to claim 1, in the form of a self-adhesive plaster matrix.

3. A transdermal therapeutic system according to claim 1, comprising a self-adhesive composition based on an optionally cross-lined acrylate or based on polyisobutenes and synthetic hydrocarbon resins.

4. A transdermal therapeutic system according to claim 2, comprising moxonidine and lauric acid.

5. A transdermal therapeutic system according to claim 4, wherein the moxonidine is micronized.

6. A transdermal therapeutic system according to claim 4, comprising 1 to 2 parts by weight of lauric acid per part by weight of moxonidine.

7. A transdermal therapeutic plaster according to claim 2, comprising 5 to 10 g of moxonidine and 7 to 20 g of lauric acid per square meter.

8. A transdermal therapeutic plaster according to claim 2, comprising 5 to 10 g of moxonidine and 7 to 15 g of lauric acid per square meter.

* * * * *